(12) United States Patent
Miyamoto et al.

(10) Patent No.: US 7,879,603 B2
(45) Date of Patent: Feb. 1, 2011

(54) METHOD FOR DIFFERENTIATING MESENCHYMAL STEM CELLS INTO STEROID-PRODUCING CELLS

(75) Inventors: Kaoru Miyamoto, Fukui (JP); Takashi Yazawa, Fukui (JP); Akihiro Umezawa, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 470 days.

(21) Appl. No.: 10/591,530

(22) PCT Filed: Feb. 18, 2005

(86) PCT No.: PCT/JP2005/002548

§ 371 (c)(1),
(2), (4) Date: Sep. 1, 2006

(87) PCT Pub. No.: WO2005/085425

PCT Pub. Date: Sep. 15, 2005

(65) Prior Publication Data

US 2008/0313752 A1    Dec. 18, 2008

(30) Foreign Application Priority Data

Mar. 3, 2004   (JP) .............................. 2004-058406

(51) Int. Cl.
*C12N 5/00* (2006.01)
*C12N 5/02* (2006.01)
*C12N 15/00* (2006.01)

(52) U.S. Cl. ...................................... 435/325; 435/455
(58) Field of Classification Search .................. 435/325, 435/455
See application file for complete search history.

(56) References Cited

FOREIGN PATENT DOCUMENTS

| | | |
|---|---|---|
| JP | 2001-245688 | 9/2001 |
| WO | WO01/83709 | 11/2001 |
| WO | WO02/22788 | 3/2002 |
| WO | WO2005/085425 | 9/2005 |

OTHER PUBLICATIONS

Val (Nuclear Receptor, 2003, vol. 1, No. 8, p. 1-23).*
Crawford (Mol. Cell. Biol., Jul. 1997, vol. 17, No. 7, p. 3997-4006).*
Gondo (Genes to Cells, 2004, vol. 9, p. 1239-1247).*
D'Ippolito, Gianluca, et al., Age-Related Osteogenic Potential of Mesenchymal Stromal Stem Cells from Human Vertebral Bone Marrow. *Journal of Bone and Mineral Research*. vol. 14, No. 7 pp. 1115-1122 (1999).
Hatano, Osamu, et al., Identical origin of adrenal cortex and gonad revealed by expression profiles of Ad4BP/SF-1. *Genes to Cells*. vol. 1, No. 7 pp. 663-671 (1996).
Luo, Xunrong, et al., The cell-specific nuclear receptor steroidogenic factor 1 plays multiple roles in reproductive function. *Philosophical Transactions of the Royal Society of London B Biological Sciences*. vol. 350, No. 1333 pp. 279-283 (1995).
Nordqvist, Katarina, et al., Sex differentiation-gonadogenesis and novel genes. *International Journal of Developmental Biology*. vol. 39, No. 5 pp. 727-736 (1995).
Supplementary European Search Report under Article 153(7) EPC corresponding to European Patent Application No. 05719267.6-2403 dated May 19, 2008.
Val, Pierre, et al., SF-1 a key player in the development and differentiation of steroidogenic tissues. *Nuclear Receptor*. vol. 1, No. 1 pp. 1-23 (2003).
Yanase, Toshihiko, et al., Differentiation and Regeneration of Adrenal Tissues: An Initial Step toward Regeneration Therapy for Steroid Insufficiency. *Endocrine Journal*. vol. 53, No. 4 pp. 449-459 (2006).
Genbank M60421.
Gojo et al., "In vivo cardiovasculogenesis by direct injection of isolated adult mesenchymal stem cells," Experimental Cell Research. vol. 288 pp. 51-59 (2003).
Hu et al., "Tissue-Specific, Hormonal, and Developmental Regulation of *SCC-LacZ* Expression in Transgenic Mice Leads to Adrenocortical Zone Characterization," Endocrinology. vol. 140, No. 12 pp. 5609-5618 (1999).
Makino et al., "Cardiomyocytes can be generated from marrow stromal cells in vitro," The Journal of Clinical Investigation. vol. 103, No. 5 pp. 697-705 (1999).
Morohashi, K., and Omura, T., "Ad4BP/FS-1, a transcription factor essential for the transcription of steroidogenci cytochrome P450 genes and for the establishment of the reproductive function," The FASEB Journal. vol. 10 pp. 1569-1577 (1996).
Okamoto et al., "Clonal heterogeneity in differential potential of immortalized human mesenchymal stem cells," Biochemical Biophysical Research Communications. vol. 295 pp. 354-361 (2002).
Okushi, Hajime, "Tissue regeneration using mesenchymal stem cells," Bioscience and Industry. vol. 60, No. 5 pp. 318-319 (2002).
Parker, K.L., and Schimmer, B.P., "Steroidogenic Factor I: A Key Determinant of Endocrine Development and Function," Endocrine Reviews. vol. 18, No. 3 pp. 361-377 (1997).
Suzuki et al., "Studies on Production of Lipids in Fungi," Journal of the Japan Oil Chemists' Society. vol. 31, No. 11 pp. 921-931 (1982) [Abstract].
Umezawa, Akihiro, "Bone Marrow Stromal Cells," Cellular Molecular Medicine. vol. 2, No. 1 pp. 17-24 (2001) [Abstract].
Umezawa, Akihiro, "In Vivo Organogenesis by Direct Injection of Isolated Adult Mesenchymal Stem Cells," Biotherapy. vol. 15, No. 2 pp. 119-125 (2001) [Abstract].
Yazawa, Takashi et al., "Preparation of steroid hormone-producing cells from bone marrow-derived mesenchymal stem cells," Folia Endocrinologica Japonica. vol. 8, No. 2 p. 457 (2004).

* cited by examiner

*Primary Examiner*—Michael C. Wilson
(74) *Attorney, Agent, or Firm*—Jenkins, Wilson, Taylor & Hunt, P.A.

(57) ABSTRACT

To control the differentiation of mesenchymal stem cells into steroid hormone producing cells. Mesenchymal stem cells can be differentiated into steroid hormone-producing cells by being stimulated by a transcriptional factor (SF-1), preferably by the transcriptional factor (SF-1) and cAMP. The present invention is a method for differentiating mesenchymal stem cells into steroid hormone producing cells, comprising stimulating the mesenchymal stem cells by the transcriptional factor (SF-1). The mesenchymal stem cells may be further stimulated by cAMP.

7 Claims, 7 Drawing Sheets

Control

SCC37

METHOD FOR DIFFERENTIATING MESENCHYMAL STEM CELLS INTO STEROID-PRODUCING CELLS

CROSS REFERENCE TO RELATED APPLICATIONS

This application is a National Stage of International Application No. PCT/JP2005/002548, filed Feb. 18, 2005, and which claims benefit of Japanese Application No. 2004-058406 filed Mar. 3, 2004.

REFERENCE TO A SEQUENCE LISTING

A Sequence Listing containing SEQ ID NOS: 1-18 is incorporated herein by reference.

1. Field of the Invention

The present invention relates to a method for differentiating mesenchymal stem cells into steroid-producing cells.

2. Prior Art

It is well known that mesenchymal stem cells have multiple differentiation potential in vivo beyond germ layers (references 1-3). It is expected that the mesenchymal stem cells will play an important role in the fields of development and regeneration, since these stem cells are easily obtained from adults and are easily subjected to established cell lines after differentiation in contrast to other embryo stem cells. The method for differentiating mesenchymal stem cells into adipocytes, chondrocytes or osteoblasts has been examined already (reference 4).

reference 1: J. Clin. Invest. 10, 697-705, 1999
reference 2: Exp. Cell. Res. 288, 51-9, 2003
reference 3: Biochem. Biophys. Res. Commun. 295, 354-61, 2002
reference 4: WO2002/022788

PROBLEMS TO BE SOLVED BY THE INVENTION

The present inventors discovered a method for controlling the differentiation of mesenchymal stem cells derived from bone marrow into steroid-producing cells. The inventors believe that the method of the present invention will become very useful method in the field of development and regeneration.

Means to Solve the Problems

The present inventors discovered that mouse bone marrow mesenchymal stem cells were differentiated into Leydig cells, steroid hormone-producing cells, when transplanted into testis (Example 4). Furthermore, it was found that a limited portion of mouse bone marrow-derived mesenchymal stem cells KUM9 were spontaneously differentiated into steroid-producing cells during culturing, and at the same time, that a transcriptional factor SF-1 was expressed (Example 5). Therefore, the inventors prepared a KUM9-derived strain, wherein SF-1 is expressed constitutively, and added a stimulation by cAMP, then the inventor found that the KUM9-derived cells stably produced steroid hormone (Examples 1 and 2). Moreover, it was confirmed that not only a gonadal steroid hormone-producing enzymes but also adrenal steroid hormone-producing enzymes are induced in a human cell line (Example 3). It is expected that these results are fundamental data in using differentiation of stem cells for medical treatment of human steroid hormone deficiency and provide a useful method for regeneration treatment.

From the above results, the inventors discovered that stimulation of mesenchymal stem cells by a transcriptional factor (SF-1), preferably with SF-1 and cAMP, enabled to differentiate the mesenchymal stem cells into steroid-producing cells and accomplished the present invention.

Namely, the present invention is a method for differentiating mesenchymal stem cells into steroid hormone-producing cells, comprising stimulating the mesenchymal stem cells by a transcriptional factor (SF-1). Furthermore, said method may comprise further stimulating the mesenchymal stem cells by cAMP.

The mesenchymal stem cells are preferably derived from bone marrow and said mesenchymal stem cells are preferably human cells.

Still furthermore, the present invention is a method for producing steroid-producing cells, comprising producing steroid producing cells by implementing said method in vitro or by transplanting the mesenchymal stem cells into a mammalian reproductive organ.

Moreover the present invention is steroid-producing cells or non-human animals containing said steroid-producing cells obtained by these method.

Advantages Of The Present Invention

The present invention provides, for the first time, a method for differentiating mesenchymal stem cells into steroid hormone-producing cells.

It will be possible to obtain a large amount of differentiated cells by transplanting stem cells into a genital gland of a non-human animal such as swine, if immune difficulties were overcome. The most important issue in regeneration medicine and others is to maintain transplanted cells keeping the differentiated state and the present invention may be applied as a tool for the development of said method. Said differentiated cells may be used as model cells for the development of regeneration medicine.

DETAILED DESCRIPTION OF THE INVENTION

Mesenchymal stem cells are derived from various interstitial cells and are able to differentiate into various cells. Mesenchymal stem cells are present not only in bone marrow but also interstitial and other tissues (e.g. in kidney, articular membrane, amnion and cord blood) of mesoderm-derived tissues. All these mesenchymal stem cells can be used in the present invention.

Mesenchymal stem cells derived from bone marrow are interstitial cells, which present in marrow stroma and maintain hematopoiesis, and said stem cells from even adult bear pluripotency of differentiating into various cells and tissues. Mesenchymal stem cells derived from bone marrow may be isolated by inserting an injection needle into an epiphysis for example, by feeding PBS into the epiphysis, by pulling out bone marrow cells, by seeding and subjecting the bone marrow cells to adhere to a plastic dish and by repeating the subculture.

The transcriptional factor (SF-1), an inducing factor used in the method of the present invention, is an orphan intranuclear receptor, which is expressed in genital and adrenal gland-type steroid hormone-producing cells, and has been known to control the transcription of steroid hormone producing-enzymes (Endocrine Reviews vol. 18, No. 3, 361-377 (1997); The FASEB Journal vol. 10 1569-1577 (1996)). Even if SF-1 is derived from different animal species, SF-1 binds to a common target DNA sequence in mesenchymal stem cells and the factor is expected to provide the same result.

cAMP exists ubiquitously in all living organism, whose intra-cellular concentration is $10^{-6}$ to $10^{-7}$ M. cAMP participates in generation of specific enzymes and metabolic control in target cells and also participates in growth and differentiation of cells. cAMP is a second messenger of LH and ACTH, which induces the expression of steroid hormone production-related enzymes in genital and adrenal glands and enhances the production of steroid hormones.

The mean to stimulate by the transcriptional factor (SF-1) and cAMP may include the direct contact of these factors with mesenchymal stem cells or the use of a vector expressing these factors.

To differentiate mesenchymal stem cells into steroid hormone-producing cells, mesenchymal stem cells may be stimulated by an inducing factor in vitro or said cells may be transplanted into a mammalian reproductive organ. In the case of in vitro induction, for example, human mesenchymal stem cells may be cultured in DMEM (Dulbecco's Modified Eagle's Medium) containing 10% FBS and mouse stem cells may be cultured in IDMM (Iscove's Modified Dulbecco's Medium) or in DMEM containing 10% FBS. The above cells are cultured in an incubator with 5% $CO_2$ at 37° C. as usual. The concentration of SF-1 is about 0.1~10 µg, preferably at 1 µg/1×10$^5$ cells, and that of cAMP is about 0.5~2.0 mM, preferably at 1 mM/1×10$^5$ cells.

When mesenchymal stem cells were transplanted into a mammalian reproductive organ, a certain factor activates the cell (in the case of organ transplantation, interaction with the surrounding cells) to express SF-1, which is considered to make these stem cells to differentiate into steroid hormone-producing cells.

In the differentiation of mesenchymal stem cells, the role of cAMP is subsidiary. Furthermore, since cAMP is necessarily present in all kind of cells with a large variety of concentrations, intracellular concentration of cAMP might be raised by some reason without adding exogenous cAMP.

As described above, steroid-producing cells may be obtained accordingly, then steroid hormone may be obtained from the steroid-producing cells.

Steroid-producing cells derived from mesenchymal stem cells include adrenal cortical cells, ovarian granulosa cells, ovarian capsular cells, testis Leydig cells, testis, Sertoli cells and others.

Obtained steroid hormones include any steroid hormone and the like, which are synthesized from cholesterol, such as progestin, androgen, estrogen, glucocorticoid and mineralcorticoid.

The following examples further illustrate the present invention, but it is not intended to limit the scope of the present invention.

Gene expression of steroid hormone synthesizing enzymes was examined by RT-PCR using the primers shown in Table 1.

TABLE 1

| Symbol | Enzyme | Primer | SEQ ID NO: |
| --- | --- | --- | --- |
| StAR | steroidogenic acute regulatory protein | F-GAAGGAAAGCCAGCAGGAGAACG<br>R-CTCTGATGACACCACTCTGCTCC | 1<br>2 |
| P450scc | cholesterol side chain cleavage enzyme | F-CGCACAGTCCAGAACAACAAGCA<br>R-CGGTTAGAGAAGGCAGGATAGAG | 3<br>4 |
| HSD3b | 3-β hydroxysteriod dehydrogenase | F-GCAGACCATCCTAGATGTCAAT<br>R-TCATCATAGCTTTGGTGAGG | 5<br>6 |
| P450c17 | 17-alpha-hydroxylase/<br>17,20-lyase | F-AAAATAATAACACTGGGGAAGGC<br>R-TGGGTGTGGGTGTAATGAGATGG | 7<br>8 |

TABLE 1-continued

| Symbol | Enzyme | Primer | SEQ ID NO: |
|---|---|---|---|
| P450c21 | steroid 21-hydroxylase | F-AGAGGATCCGCTTGGGGCTGC | 9 |
|  |  | R-GGAGAATTCCTTATGGATGGC | 10 |
| P4501 1b1 | steroid 11-beta-hydroxylase | F-TCACCAAATGTATCAAGAATGTGT | 11 |
|  |  | R-CCATCTGCACATCCTCTTTCTCTT | 12 |
| P4501 1b2 | aldosterone synthase | F-CCAACAGATGTATCTGGAAGGTGC | 13 |
|  |  | R-CCATCTGCACATCCTCTTGCCTCA | 14 |
| GAPDH | glyceraldehyde phosphate dehydrogenase | F-ACCACAGTCCATGCCATCAC | 15 |
|  |  | R-TCCACCACCCTGTTGCTGTA | 16 |

EXAMPLE 1

Figure 1:
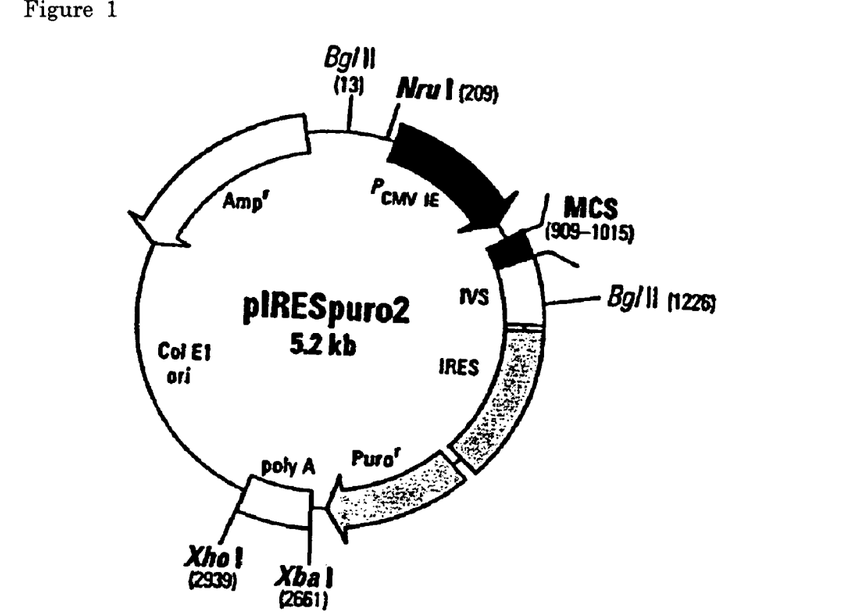
FIG. 1 shows pIRES-puro2 vector.

The coding region (Nucleotides 1~1389 of SEQ ID NO: 17) of rat SF-1 gene (Gene Bank NM_053344, SEQ ID NO:17) was integrated in pIRES-puro2 vector (Clontech, FIG. 1). KUM9 cells (obtained from Department of Reproductive Biology, National Research Institute for Child Health and Development), an established adult mouse-derived mesenchymal stem cell line, were transfected with said vector after linearized with Nru I and were selected in a medium containing puromycin (2 μg/ml) at 48 hrs after the transfection. The resistant colonies remained for 2 weeks in the medium were picked up and were cloned.

Figure 2:
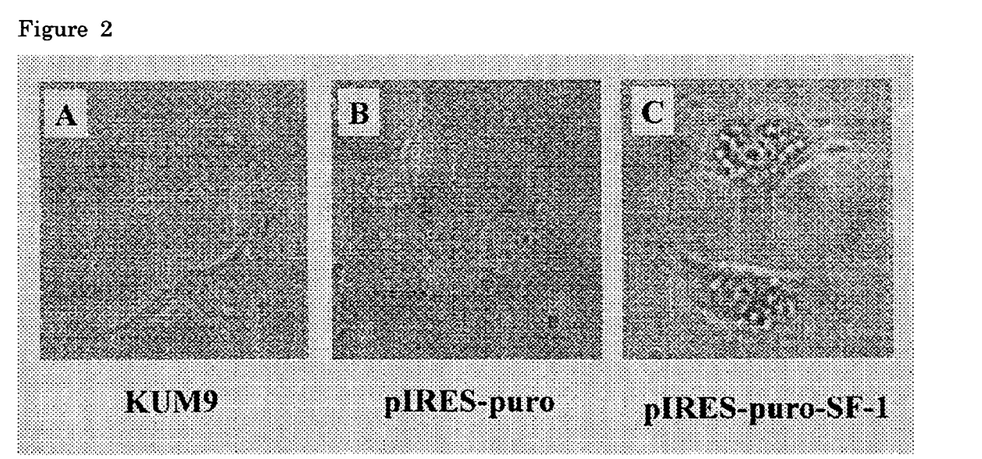
FIG. 2 shows KUM9 cells (A) and KUM9 cells stably transfected with parent vector (B) and with SF-1 expressing vector (C).

Those clones transfected with parent vector pIRES-puro (FIG. 2B) showed similar morphology to that of KUM9 without transfection (FIG. 2A). In contrast, a large number of fat droplets, conceivably containing cholesterol, i.e. a precursor of steroid hormones, were observed intracellularly in clones (SF-7 and SF-9) expressing SF-1 (FIG. 2C).

Figure 3:
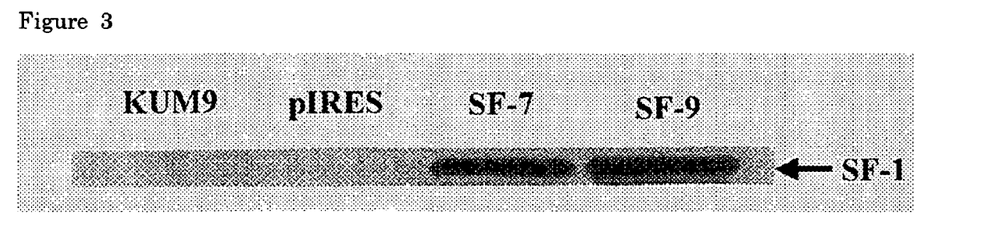
FIG. 3 shows the western blotting showing SF-1 protein detected in various cell lines. SF-7 and SF-9 are the 7th and 9th cell lines, respectively, which are established by transduction of SF-1.

Proteins were extracted from each clone (SF-7 and SF-9), were examined the expression of SF-1 protein by Western blotting and SF-1 protein was detected (FIG. 3).

Furthermore, gene expression of steroid hormone synthesizing enzymes in these cells was examined by RT-PCR and the expression of P450scc was confirmed.

EXAMPLE 2

Figure 4:
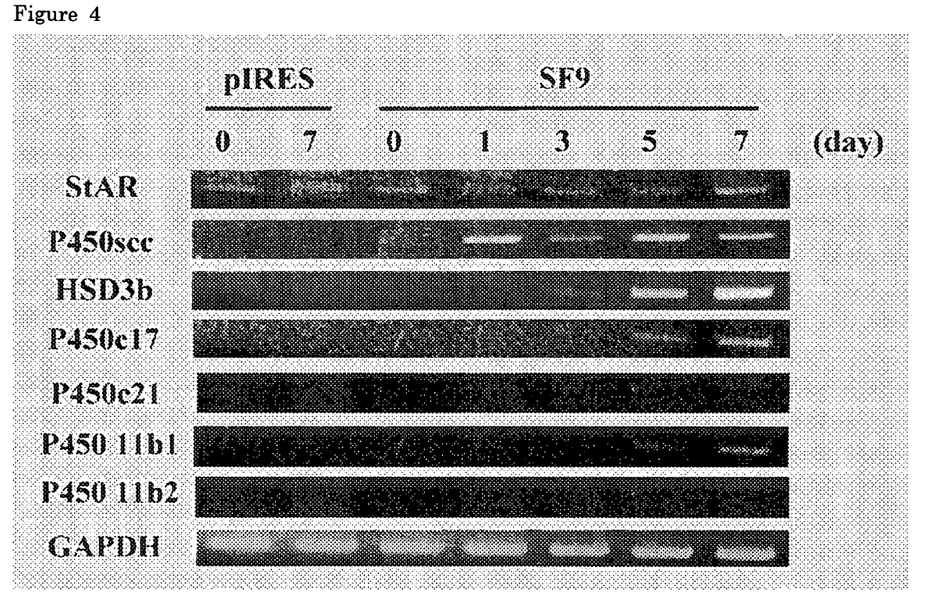
FIG. 4 shows the result of RT-PCR for RNA isolated from KUM9 cells, which are stably transduced with parent vector (pIRES) and SF-1 (SF-9) and are cultured for 7 days in the presence of cAMP. Days shown on the upper row are days until extraction of RNA after the addition of cAMP. HSD3b (3b-HSD) expresses on the 3rd day and P450c17 and P450c11b1 express on the 5th day.

The cloned cells (SF-9), wherein expression of SF-1 was observed in example 1, were cultured for 7 days in the presence of cAMP (1 mM, Sigma). On 1, 3, 5 and 7 days after addition of cAMP, RNA was extracted from said cells and was examined the gene expression by RT-PCR. For comparison, the same procedures were performed for cloned cells using the parent vector pIRES as a negative control. The results show that the expression of p450scc was induced after 1 day, HSD3b1 was induced after 3 days and furthermore p450c17 was induced after 5 days (FIG. 4).

Figure 5:
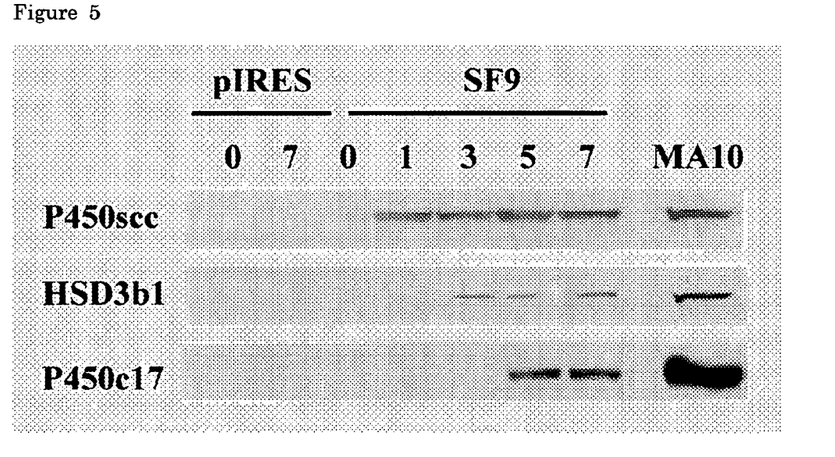
FIG. 5 shows the western blotting for proteins extracted from the cells cultured under a condition similar to that described in FIG. 4. Proteins from MA10-derived cells originated from mouse Leydig cells are used as a positive control.

The result of Western blotting shows that the expression of these enzyme proteins was induced similar to that of mRNA (FIG. 5).

Moreover, according to these results, those cells without transfection with SF-1 (pIRES-puro) do not express steroid hormone-producing enzymes by the addition of cAMP and do not produce steroid hormone. These facts could be interpreted as that only cAMP could not induce differentiation into steroid hormone-producing cells.

The interpretation depicts that SF-1 is an essential factor to differentiate mesenchymal stem cells into steroid hormone producing cells and cAMP is a cofactor.

Figure 6:
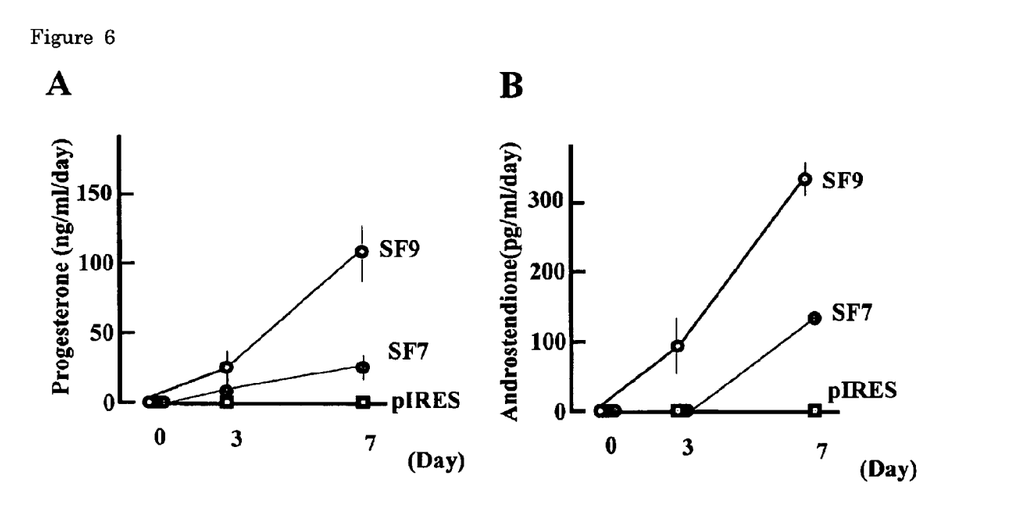
FIG. 6 shows quantification by RIA of secreted steroid hormone, which is obtained by the recovery of supernatant of the medium used for the cells cultured under a condition similar to that described in FIG. 4. The amount of hormone produced within 24 hrs was determined by changing culture medium to fresh medium on the day before the each indicated day.

The output of steroid hormone was measured by radioimmuno assay (RIA) after recovery of culture medium on the 3rd day and 7th day. According to the results, progesterone and androgen were detected on the 3rd day and 7th day, respectively, in parallel to the results of expression of mRNA and proteins (FIG. 6) in the group of cells added with cAMP. Not only the induction of steroid synthesizing enzyme but also the synthesis of androstendione, a kind of androgenic hormone, was confirmed.

Figure 7:
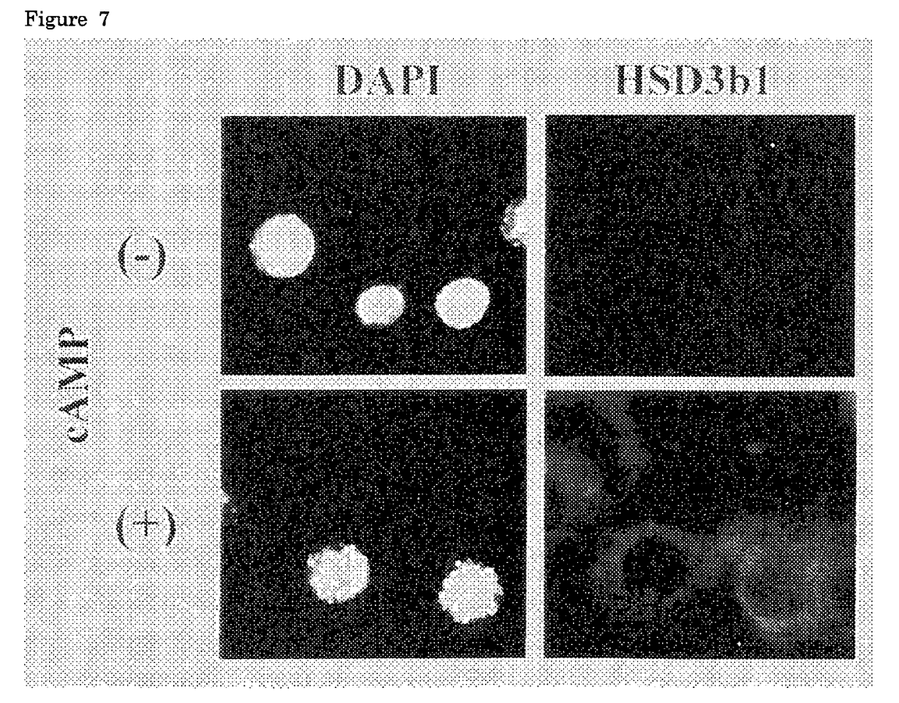
FIG. 7 shows immunostaining by anti-3β HSD I antibody of SF-9 cells, which are fixed before adding cAMP (−) or after culture for 7 days in the presence of cAMP (+). DAPI (4',6-Diamidino-2-phenylindole, dihydrochloride) is a dye marker for DNA and shows the intracellular localization of nucleus.

Immunostaining of HSD3b1 shows that all cells are positive (FIG. 7).

The results of examples 1 and 2 show that forced expression of SF-1 leads mesenchymal stem cells derived from bone marrow to differentiate into steroid hormone-producing cells.

EXAMPLE 3

Figure 8:
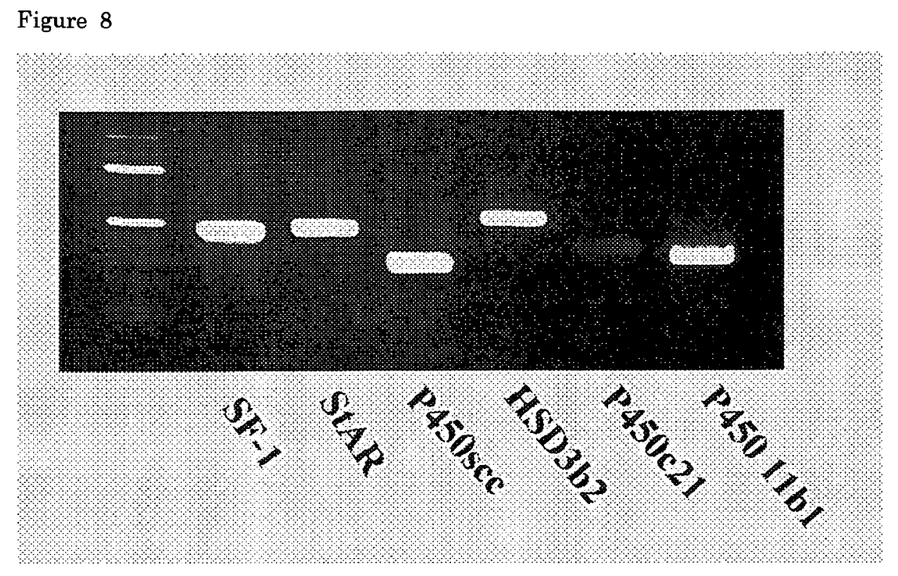
FIG. 8 shows the result of RT-PCR for RNA extracted from hMSC E6/E7 cells, which is derived from human bone marrow mesenchymal stem cells, are stably transduced with SF-1, and are cultured for 7 days in the presence of cAMP.

Induction of steroid hormone-producing cells for human cells was examined in an experiment similar to example 2 using human derived cells. Human bone marrow mesenchymal stem cells hMSCE6/E7 (gifted from Field of Clinical Application, Institute for frontier Medical Sciences, Kyoto University) were transfected with said pIRES-puro-SE-1 vector by calcium phosphate method. At 48 hrs after transfection, cells were selected in a medium containing puromycin (0.3 μg/ml), puromycin resistant colonies were picked up after 2 weeks and they were cloned. After 7 days culture in the presence of cAMP, RNA was isolated and gene expression was examined by RT-PCR.

hMSC cells stably expressing pIRES-puro-SF-1 did not show morphological change as observed for KUM9 cells (FIG. 2A-C). However, analysis of gene expression by RT-PCR shows the induction of expression of a group of steroid hormone synthesizing genes such as StaR, P450scc and 38-HSD. Furthermore, addition of cAMP induced the expression of P450 c21 and P450 11b1, glucocorticoid producing enzymes in adrenal cortex (FIG. 8).

These results show that human bone marrow-derived mesenchymal stem cells were differentiated into steroid hormone-producing cells.

EXAMPLE 4

In this example, bone marrow-derived mesenchymal stem cells were transplanted into testis. Bone marrow cells were isolated from epiphysial region of os longum from limbs of 5 w.o. male Green rat by insertion of a 26-gauge needle for syringe and by filling of PBS. After red blood cells were disrupted by osmotic shock, said cells were seeded at 5×10⁷/100 ml dish containing α-MEM medium fortified with 20%

FBS. After 24 hrs, the medium was changed to remove non-adherent cells. After 3 days, cells were trypsinized by 0.25% trypsin, subcultured, and cultured for further 1 week. These procedures lead to concentrate mesenchymal stem cells among various bone marrow-derived cells. After confluent cells were trypsinized, $1\times10^6$ cells were suspended in 50 µl PBS and were injected into testis of 3 w.o. male Sprague Dawley rat (Japan Charles River Co.).

After 3 weeks, the testis was removed, observed under inverted microscopy and fixed by 4% para-formaldehyde. Frozen sections were prepared and used for immunohistochemical method. Double staining was performed using rabbit anti-rat P450scc antibody (CHEMICON) and mouse anti-GFP antibody (MBL) for the first antibody and Cy3-conjugated anti-rabbit IgG antibody (SIGMA) and FITC-conjugated anti-mouse IgG (SIGMA) as the second antibody.

Figure 9:
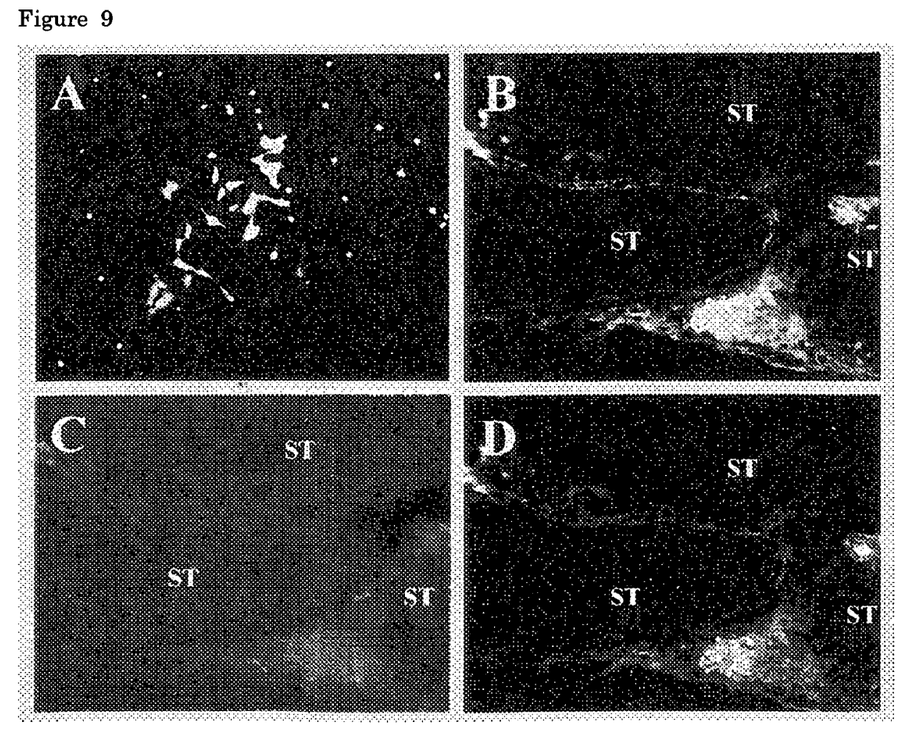
FIG. 9 shows testis transplanted with mesenchymal stem cells derived from bone marrow. ST shows seminiferous tubule.

GFP positive cells, possibly derived from Green rat bone marrow, were observed easily under inverted fluorescent microscopy and were detected in testis at 3 weeks after transplantation (FIG. 9A). Therefore, it was found that transplanted cells adhered to host testis. To examine whether these cells were differentiated into steroid hormone producing cells (Leydig cells), double immunostaining using anti-GFP (FIG. 9B) and anti-P450scc (FIG. 9C) was performed. Since most of P450scc positive cells were also GFP positive, Green rat bone marrow-derived cells were found to be differentiated into Leydig cells.

EXAMPLE 5

Stem cells could not completely be clonized by the method of example 4 because of the contamination of macrophage cells. Therefore, an experiment was performed to examine whether KUM9 cells, an established adult mouse-derived mesenchymal stem cells, has a potency to be differentiated in vitro into steroid hormone-producing cells.

P450scc (a side chain cleavage enzyme) is an enzyme, which is localized on mitochondrial inner membrane and catalyzes a reaction degrading cholesterol into pregnenolone. Since the above reaction is a necessary procedure in all steroid hormone production, P450scc is expressed in all steroid hormone-producing cells. The group of Chung et al. prepared and used transgenic mice with a visual reporter gene Lac Z and showed that 2.3 Kbp of 5' upstream region in human P450scc gene (Gene Bank M60421) controls the expression of P450scc gene in steroid hormone-producing cells in genital and adrenal gland (Endocrinology, 140:5609

18, 1999). Therefore, preparation of stem cells, wherein the visual reporter gene expresses by the control of the said 5' upstream region, conceivably enables to detect the differentiation into steroid hormone-producing cells.

Figure 10:
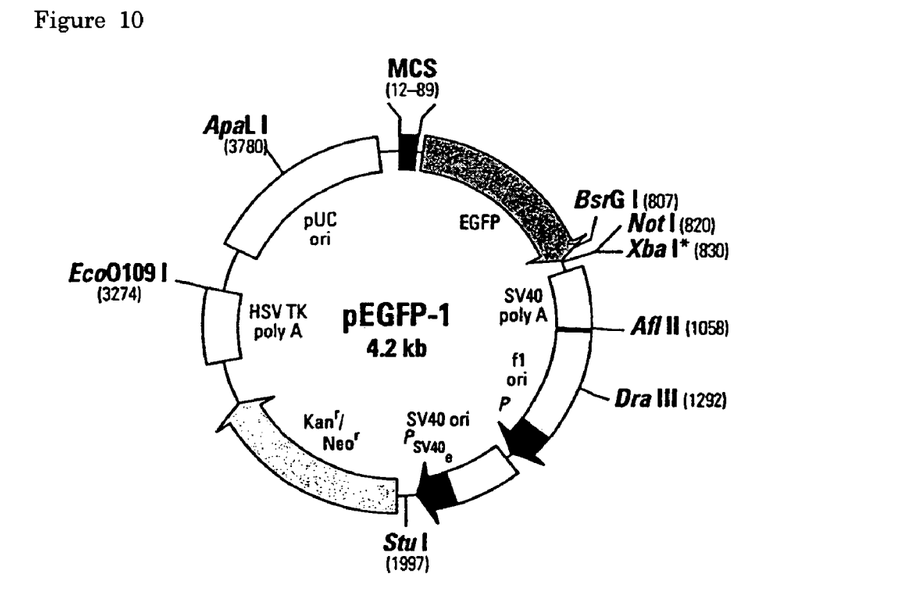
FIG. 10 shows pEGFP-1 vector.
Figure 11:
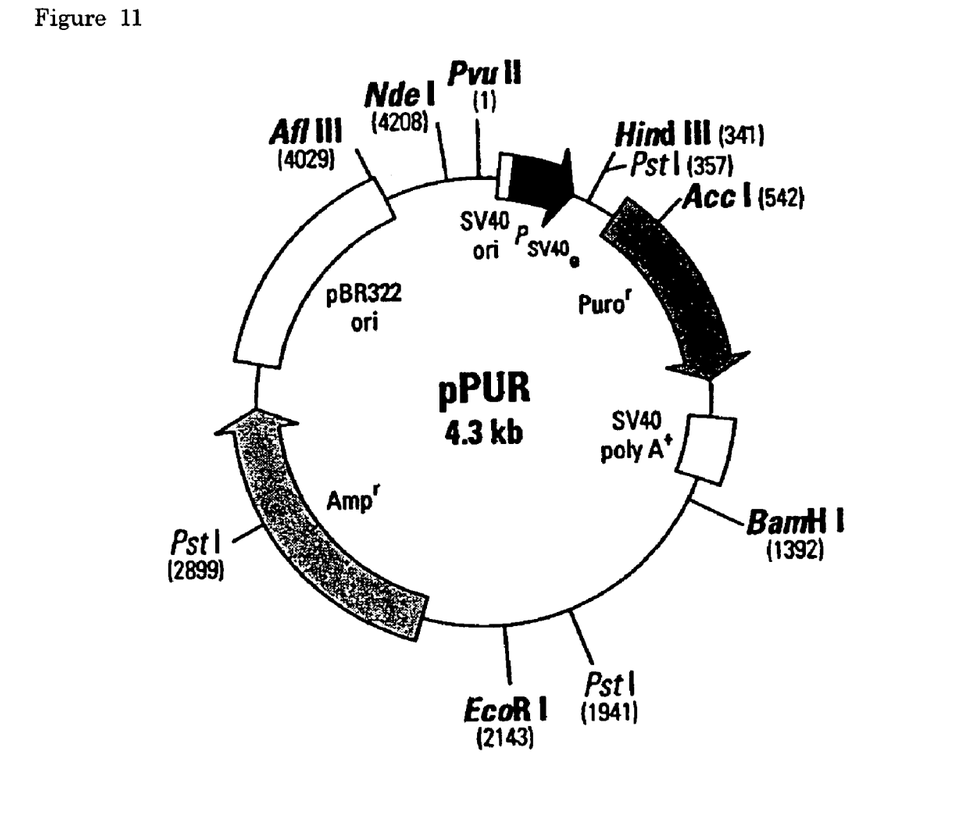
FIG. 11 shows pPUR vector.

Therefore, P450scc gene (Gene Bank M60421, SEQ ID NO: 18) was integrated into the upstream of EGFP protein coding region of pEGFP-1 vector (FIG. 10, Clontech) and the vector was fused with pPUR vector (FIG. 11, Clontech) coding puromycin resistant gene.

Said synthetic vector, after linearized with ApaL I, was transfected into KUM9 cells (Gifted from Department of Reproductive Biology, National Research Institute for Child Health and Development), derived from mouse bone marrow mesenchymal stem cells by lipofection. Since fluorescent GFP expresses at the time of expression of P450scc in these cells, spontaneously differentiated KUM9-derived steroid-producing cells could be separated by flow cytometer using fluorescence as a probe.

At 48 hrs after the separation, cells were selected in the medium containing puromycin (2 µg/ml) and resistant colonies after 2 weeks was clonized by a limiting dilution method.

Figure 12:
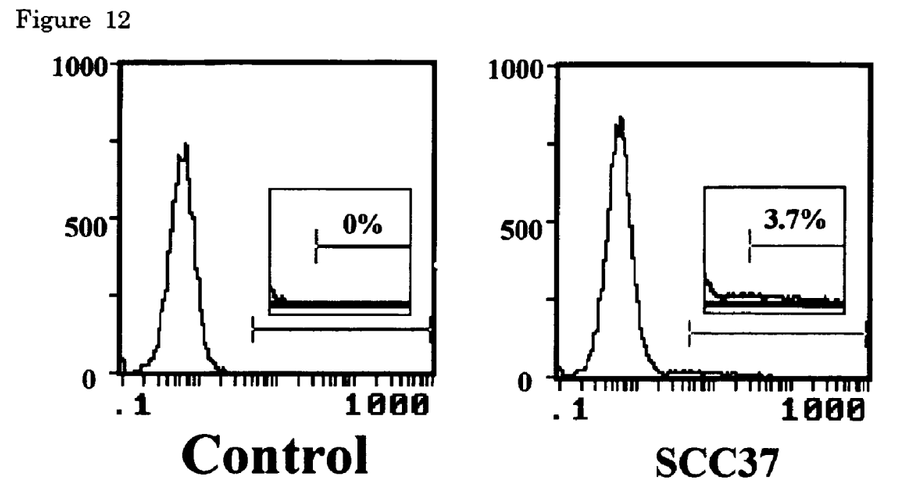
FIG. 12 shows the charts of flow cytometry for a GFP positive clone.

GFP positive cells were detected in 2 clones out of isolated 250 clones during growing phase of these cells under inverted fluorescence microscopic observation. GFP positive and negative cells were separated by flow cytometer for said 2 clones, wherein a lot of GFP positive cells were found, and GFP positive cells were 2~5% (FIG. 12).

Figure 13:
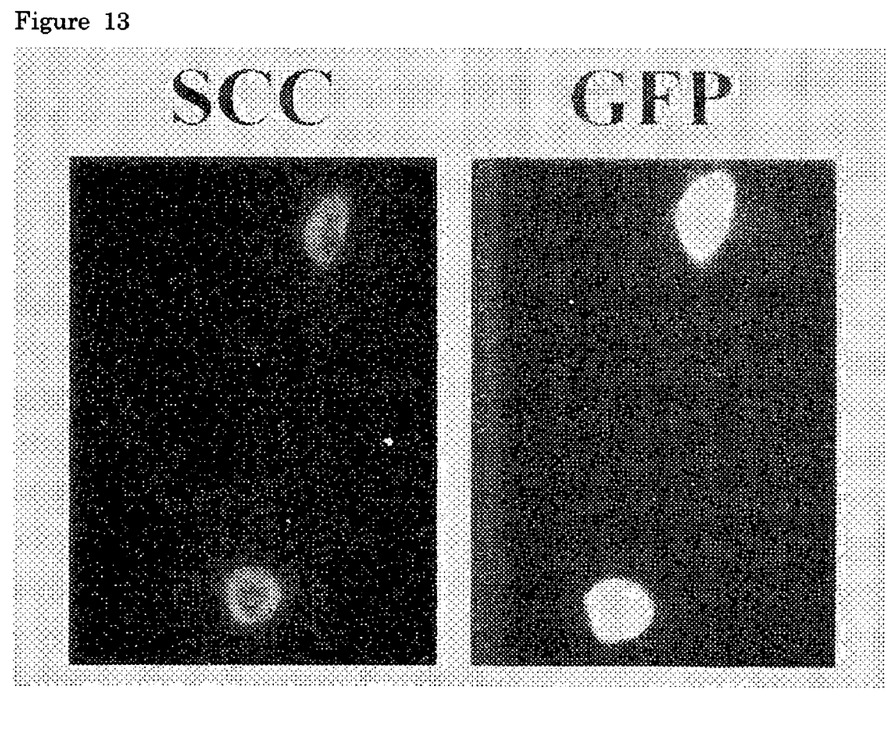
FIG. 13 shows immunostaining of P450scc in GFP positive cells.

Furthermore, immunostaining of P450scc for GFP positive cells confirmed that GFP positive cells were also P450scc positive (FIG. 13).

Figure 14:
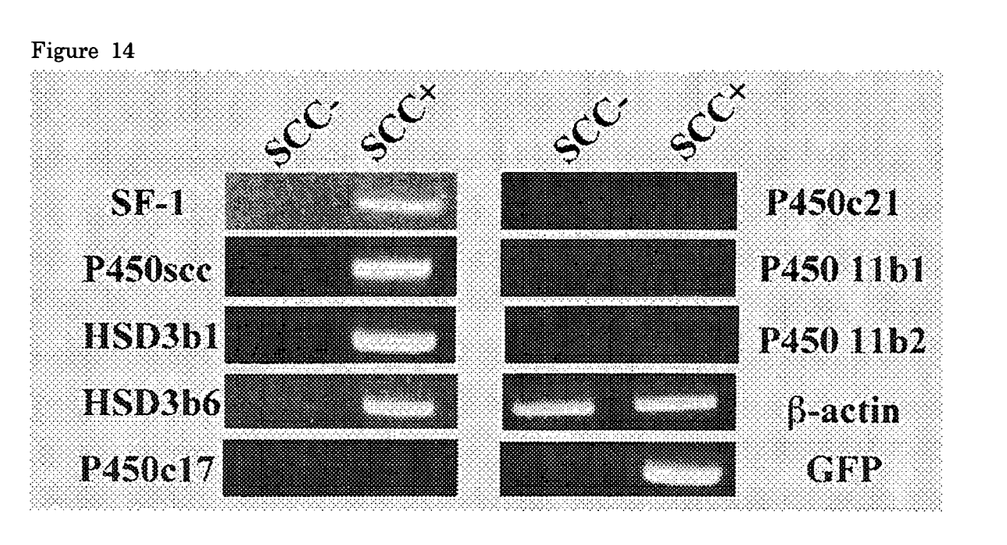
FIG. 14 shows the results of RT-PCR of various enzymes in GFP positive (scc+) and negative (scc−) cell fractions.

Moreover, GFP positive (scc+) and negative (scc−) cells were separated by a cell sorter, total RNA was extracted from the separated cells and cDNA was prepared by reverse transcription reaction using reverse transcriptase. RT-PCR was performed using a specific primer for each gene. The expression of mRNA of P450scc gene was observed in GFP positive cells (scc+) (FIG. 14). Additionally, the transcriptional factor SF-1 was expressed in said cells isolated. Still furthermore, examination of the expression of genes involved in steroid hormone production revealed that the expression of 3β-HSD gene of both genital and adrenal gland type (HSD3b1) and placental type (HSD3b6) was observed.

From these results, it was interpreted that the transplantation induced the expression of SF-1 in stem cells, and that these stem cells differentiated into steroid hormone-producing cells on contact with SF-1.

What is claimed is:

1. A method for differentiating mesenchymal stem cells into cells that produce steroid hormone-producing enzymes, comprising stimulating the mesenchymal stem cells, in the presence of cAMP, by transfecting the cells with a vector encoding a steroidogenic factor 1 (SF-1) wherein the steroid hormone-producing enzymes are selected from the group consisting of p450scc, p450c17, HSD3b1, StAR, 3β-HSD, p450 c21, p450 11b1, and HSD3b6, wherein progesterone, androstenedione, or androgen is produced.

2. The method of claim 1, wherein the mesenchymal stem cells are derived from bone marrow.

3. The method of claim 2, wherein the mesenchymal cells are derived from human.

4. The method of claim 1 wherein the stimulating by SF-1 in the presence of cAMP is implemented in vitro.

5. The method of claim 4 further comprising culturing the cells that produce steroid hormone-producing enzymes and recovering steroid hormone from the culture medium.

6. A method for differentiating mesenchymal stem cells into steroid hormone-producing cells, comprising stimulating the mesenchymal stem cells, in the presence of cAMP, by transfecting the cells with a vector encoding a steroidogenic factor 1 (SF-1), wherein said hormone is selected from the group consisting of progesterone, androgen, and androstenedione.

7. A method for differentiating mesenchymal stem cells comprising stimulating the mesenchymal stem cells, in the presence of cAMP, by transfecting the cells with a vector encoding SF-1 wherein steroid hormone-producing enzymes selected from the group consisting of p450scc, p450c17, HSD3b1, StAR, 3β-HSD, p450 c21, p450 11b1, and HSD3b6, wherein progesterone, androstenedione, or androgen is produced are produced.

* * * * *

SEQUENCE LISTING

<160> NUMBER OF SEQ ID NOS: 18

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaaggaaagc cagcaggaga acg                                            23

<210> SEQ ID NO 2

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctctgatgac accactctgc tcc                                              23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcacagtcc agaacaacaa gca                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggttagaga aggcaggata gag                                              23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcagaccatc ctagatgtca at                                               22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcatcatagc tttggtgagg                                                  20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaaataataa cactggggaa ggc                                              23

<210> SEQ ID NO 8
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgggtgtggg tgtaatgaga tgg                                          23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agaggatccg cttggggctg c                                            21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggagaattcc ttatggatgg c                                            21

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcaccaaatg tatcaagaat gtgt                                         24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccatctgcac atcctctttc tctt                                         24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccaacagatg tatctggaag gtgc                                         24

<210> SEQ ID NO 14
<211> LENGTH: 24
<212> TYPE: DNA
```

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
ccatctgcac atcctcttgc ctca                                          24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
accacagtcc atgccatcac                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tccaccaccc tgttgctgta                                               20

<210> SEQ ID NO 17
<211> LENGTH: 1389
<212> TYPE: DNA
<213> ORGANISM: Rattus norvegicus

<400> SEQUENCE: 17

| | | | | | |
|---|---|---|---|---|---|
| atggactatt | cgtacgacga | ggacctggac | gagctgtgtc | cagtgtgtgg | tgacaaggtg | 60 |
| tcgggctacc | actacgggct | gctcacgtgc | gagagctgca | agggcttctt | caagcgcaca | 120 |
| gtccagaaca | acaagcatta | cacgtgcacc | gagagtcaga | gctgcaaaat | cgacaagacg | 180 |
| cagcgtaagc | gctgtccctt | ctgccgcttc | cagaagtgcc | tgacggtggg | catgcgcctg | 240 |
| gaagctgtgc | gtgctgatcg | aatgcggggc | ggccggaaca | agtttgggcc | catgtacaag | 300 |
| agagaccggg | ccttgaagca | gcagaagaaa | gcacagattc | gggccaatgg | cttcaaactg | 360 |
| gagaccggac | caccgatggg | ggttcccccg | cccccccctc | ccccaccgga | ctacatgtta | 420 |
| ccccctagcc | tgcatgcacc | ggagcccaag | gccctggtct | ctggcccacc | cagtgggccg | 480 |
| ctgggtgact | tggagccccc | atctctgccc | atggccgtgc | ctggtcccca | cgggcctctg | 540 |
| gctggctacc | tctatcctgc | cttctctaac | cgcaccatca | agtctgagta | tccagagccc | 600 |
| tacgccagcc | cccctcaaca | gccagggcca | ccctacagct | atccggagcc | cttctcagga | 660 |
| gggcccaatg | taccagagct | catattgcag | ctgctgcaac | tagagccaga | ggaggaccag | 720 |
| gtgcgtgctc | gcatcgtggg | ctgcctgcag | gagccagcca | aaagccgccc | tgaccagcca | 780 |
| gcgcccttca | gcctcctctg | caggatggcg | gaccagacct | ttatctccat | tgtcgactgg | 840 |
| gcacgaaggt | gcatggtatt | taaggagctg | gaggtggctg | accagatgac | actgctgcag | 900 |
| aactgctgga | gtgagctgct | ggtgctggac | cacatctacc | gccaggtcca | gtacggcaag | 960 |
| gaagacagca | tcttgctggt | cactggacag | gaggtggagc | tgagcacggt | ggctgtgcag | 1020 |
| gctggctccc | tgctgcacag | cctggtgctg | cgggcacagg | agttggtgct | gcagctgcat | 1080 |

| | |
|---|---|
| gccctgcaac tggaccgcca ggagtttgtc tgtctcaagt tcctcatcct cttcagcctc | 1140 |
| gatgtgaaat tcctgaacaa ccacagcctg gtaaaggacg cccaggagaa ggccaacgcc | 1200 |
| gccctgctgg attacacctt gtgtcactac ccacactgcg gggacaaatt ccagcagttg | 1260 |
| ctattgtgcc tggtggaggt gcgggcactg agcatgcagg ccaaggagta tctgtaccat | 1320 |
| aagcatttgg gcaacgagat gccccgcaac aaccttctca ttgagatgct gcaggccaag | 1380 |
| cagacttga | 1389 |

<210> SEQ ID NO 18
<211> LENGTH: 2393
<212> TYPE: DNA
<213> ORGANISM: Homo sapiens

<400> SEQUENCE: 18

| | |
|---|---|
| aagcttcagg gatggcagcc gcttgtgaga accctgagc atgagccact cagccaccca | 60 |
| gccacccagt cacccagcca cccagccacc cagtcaccca gaaaagctgc tcctgggtgc | 120 |
| tgcaccctcg gaagctgtga gataataaac atttattgtt ttaagccact aaattttggg | 180 |
| ataatttgtt aagcagcagt aaacagctaa tacattcagc cttgtttgga gtgagtgatg | 240 |
| tgtttctgga agctctttca gagaagtgag ggagctattc tcccagaagc cacagcaaac | 300 |
| ctttccctgt gtttcattgg cccaaactgg atcggctggc ctatgctgtg atgtgaccat | 360 |
| ggcgattgga gaggatgagg caataacctc cagcctgggc cacttctggg gaggcggtca | 420 |
| gtgcccacaa cactgggga ggtgcggagg cctgaacgga gttgggtg gctgccaaga | 480 |
| ggaccacaag ttcttccatg ccacatcgat tagggctcct tctgagggag gaatgtgggg | 540 |
| ctgcgtagaa caatgggatt gactttaagt cagaaagtta taaatgtcac ctcagtgctg | 600 |
| agacccttgg aggaaaaact agtccttgga agactgcttt tcttgtggaa gctcatcacc | 660 |
| ctgccgctgc tcgtgagaca ctgccttcct tggctgatgt cattccaggc tcaaggtcat | 720 |
| catggaggca aaacaggctt tctcatactc tctttatcag aaggttcatg actgatgagg | 780 |
| tagtggtcac tccagcggga agagcaacaa ccactcttga taagtacttt ttttttttct | 840 |
| tctaaaaact gttgctctaa atttgttgaa agtggttcaa cagtattgga gtctggggtc | 900 |
| aagtggctgt gtaaggacaa cttttgccat tgtgggtgat ctatgggctg acacatacaa | 960 |
| cagaagaggc caggaggatg tcactcgtgt gtgtgtgtgt gtgtgtgtgt gtgttggtaa | 1020 |
| cagctctatt gagatataat tcacacacca tacattcacc catttaaagt atgcaattca | 1080 |
| atggcttta gtgtatagag agttgttcaa taattaccac atatctttag aatattttca | 1140 |
| ttttcatcat cctaagaatc cctacacact ttatgtccca tcctctaatt cctctatccc | 1200 |
| cctagctcta agcaaccacc agtctatttt ctgtctgtta gatgtgtgtt ttaaatgcct | 1260 |
| tatttgccag aaaataagat tttggggaaa aaagcaaga agtaccttcc aatgataagt | 1320 |
| ataaggtata gtgtagattg ctgtcatgaa atgctctaca tggcacatgt atgttttctg | 1380 |
| acctacacat ttttaccaag tgggctgtaa ttttgttgaa atgacttgaa aactctacag | 1440 |
| gtgactgacc cttgttgttt gggaaagtgg taggtgcagg gtgatggggg gtgggtgtgg | 1500 |
| gggctgacct gggctggaag gatgggtctg gggatatgat atgatgggag ggggtatgga | 1560 |
| agcagctctg aggggtttgc agcacagatc aagtgtgtgg acaggaaga gctgacatcc | 1620 |
| tgagttccgg atggcaacca gatttgccaa ggtcttagag tgtgtccaga gtggagcctg | 1680 |
| accacagacc tcagctcaag ggacccgagag cccctctgag tcagctgtac tgaattacag | 1740 |
| ccccaaatct gggtcaactg gggagagacg acgaggatta gggttccaag gtgaaactgt | 1800 |

```
                                            -continued gccattgcgc tccagcctgg gcaacaagaa tgaaactctc ttaaaataaa ataaaataaa    1860
atagcctaag gatgcatttc tcagaactta tccctgttgt tcaatgatgt gtgtctatac    1920
agtggggcca taactaagac gtatgttgcc caagctggca agatagctct gaccttctct    1980
tgggcccctc atttccccca aacacaggtt gtctgcagtc ttgaccaatg gctgccaggg    2040
catggactcc gctgcagggg ccagtgggag gccccagctc aggcaaaagc acaggcagat    2100
atttcaggag tctgctaggg ctggcactga gggcagagac agagggtct ccctgtcctt     2160 tggagaacct cacgctgcag aaattccaga ctgaaccttg ataccgagta ggggaggagc    2220
tgtctgcggg tttgagcctg cagcaggagg aaggacgtga acattttatc agcttctggt    2280
atggccttga gctggtagtt ataatcttgg ccctggtggc ccagggctac agtcatccta    2340
gcagtccccg ctgaagtgga gcaggtacag tcacagctgt ggggacagca atg           2393
```